United States Patent [19]

Yoshida et al.

[11] Patent Number: 5,466,816
[45] Date of Patent: Nov. 14, 1995

[54] PROCESS FOR PREPARATION OF AZOLYLMETHYLCYCLOALKANOL DERIVATIVES

[75] Inventors: Eyji Yoshida; Nobuyuki Kusano; Satoru Kumazawa, all of Iwaki, Japan

[73] Assignee: Kureha Chemical Industry Co., Ltd., Tokyo, Japan

[21] Appl. No.: 337,275

[22] Filed: Nov. 10, 1994

[30] Foreign Application Priority Data

Nov. 11, 1993 [JP] Japan ................................. 5-305816

[51] Int. Cl.$^6$ ................. C07D 249/08; C07D 233/60
[52] U.S. Cl. ................. 548/267.8; 548/267.2; 548/267.4; 548/268.6; 548/335.5; 548/336.1
[58] Field of Search ............. 548/267.2, 267.4, 548/267.8, 268.6, 335.5, 336.1

[56] References Cited

U.S. PATENT DOCUMENTS

| | | | |
|---|---|---|---|
| 4,670,454 | 6/1987 | Janssen et al. | 514/383 |
| 4,938,792 | 7/1990 | Kumazawa et al. | 71/92 |
| 5,194,444 | 3/1993 | Seele et al. | 514/383 |
| 5,256,683 | 10/1993 | Hutt et al. | 514/383 |

FOREIGN PATENT DOCUMENTS

| | | |
|---|---|---|
| 0324646 | 7/1989 | European Pat. Off. . |
| 0329397 | 8/1989 | European Pat. Off. . |
| 0413448 | 2/1991 | European Pat. Off. . |

OTHER PUBLICATIONS

Y. Izumi et al., "Liquid–Phase Organic Reactions Catalyzed by Inorganic Solid Acids and Bases", *Chemical Abstracts* 117:654 (1992).

*Primary Examiner*—Patricia L. Morris
*Attorney, Agent, or Firm*—Testa, Hurwitz & Thibeault

[57] ABSTRACT

A process for preparing a derivative of azolylmethylcycloalkanol of the following formula (I) comprising, providing a solid-liquid two-phase mixture of a cycloalkanone derivative of formula (II), an azole compound of formula (III), a metal oxide of formula (IV), and an organic solvent, and adding a sulfonium compound of formula (V) to said solid-liquid two-phase mixture under heating while stirring,

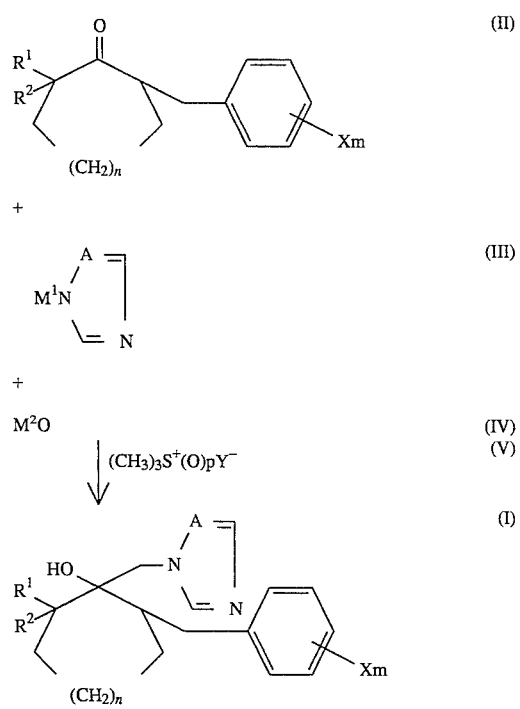

wherein $R^1$ and $R^2$ individually represent a hydrogen atom or an alkyl group; X is a halogen atom, an alkyl group, a haloalkyl group, a phenyl group, a cyano group, or a nitro group; m is an integer of 0 to 5 (when m is 2 or larger, Xs may be either the same or different); n is an integer of 0 to 2; A represents a nitrogen atom or a group CH; $M^1$ represents an alkali metal atom or an alkaline earth metal atom; $M^2$ represents an alkaline earth metal atom, a zinc atom, or two alkali metal atoms; Y represents a halogen atom or a $C_1$–$C_4$ alkoxysulfonyloxy group; and p denotes an integer of 0 or 1.

4 Claims, No Drawings

PROCESS FOR PREPARATION OF AZOLYLMETHYLCYCLOALKANOL DERIVATIVES

BACKGROUND OF THE INVENTION

1. Field of the Invention

The present invention relates to a process for preparing a derivative of azolylmethylcycloalkanol which is useful as an active ingredient of antifungal compositions.

2. Description of Background Art

As a process for preparing azolylmethylcycloalkanol derivatives, U.S. Pat. No. 4,938,792, for example, discloses a process comprising preparing a methylenecyclopentane derivative from a cyclopentanone derivative, epoxidizing the methylenecyclopentane derivative to produce an oxirane derivative, and reacting the oxirane derivative with an azole compound, according to the following reaction formula (a).

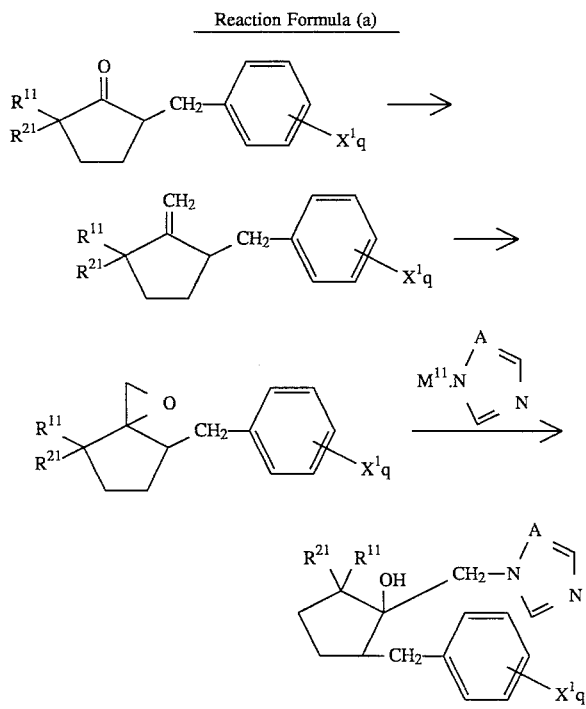

Reaction Formula (a)

wherein $R^{11}$ and $R^{21}$ respectively represent hydrogen atom or $C_1$–$C_5$ alkyl group; $X^1$ represents halogen atom, $C_1$–$C_5$ alkyl group, or phenyl group; q represents an integer of 0 to 2; A represents nitrogen atom or CH group; and $M^{11}$ represents hydrogen atom or alkali metal atom, provided that $R^{11}$ is not hydrogen atom when $R^{21}$ is hydrogen atom.

EP 329397 discloses a method for reacting a cyclopentanone derivative, sulfonium methylide or sulfoxonium methylide, and an alkali metal salt of azole compound or an azole compound and a base, in a polar solvent containing an amide bond or dimethylsulfoxide, or in a mixed solvent of this polar solvent and an alcohol, according to the following reaction formula (b); and a method for reacting a cyclopentanone derivative and an alkali metal salt of azole compound or an azole compound and a base, while intermittently adding trimethylsulfonium halide or trimethylsulfoxonium halide to a solution of these reactant compounds.

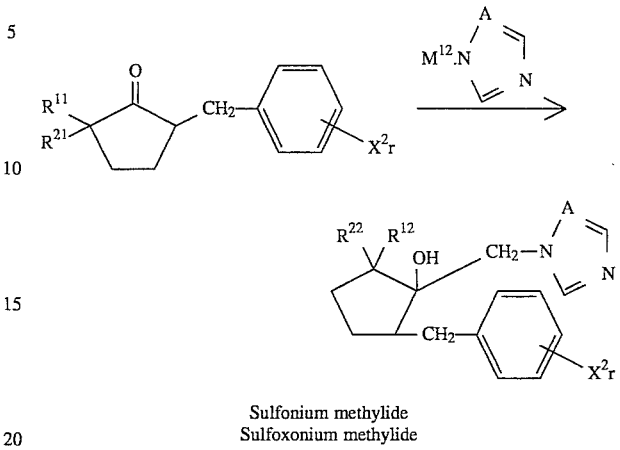

Reaction Formula (b)

Sulfonium methylide
Sulfoxonium methylide wherein $R^{12}$ represents hydrogen atom or $C_1$–$C_5$ alkyl group; $R^{22}$ represents hydrogen atom or $C_1$–$C_2$ alkyl group; $X^2$ represents halogen atom, $C_1$–$C_4$ alkyl group, phenyl group, and the like; A represents nitrogen atom or CH group; $M^{12}$ represents hydrogen atom or alkali metal atom; and r represents an integer of 1 to 5.

As a method for epoxidation of ketones or aldehydes, Tetrahedron Lett., 23, 5283–5286 (1982) describes that ketones (acetophenone, 2-acetylfurane, etc.) can be epoxidized by a solid-liquid two-phase reaction using trimethylsulfonium iodide, potassium hydroxide, acetonitrile, and a small amount of water. Further, Tetrahedron, 1985, 1259–1266 describes that benzalehyde can be epoxidized in the absence of a solvent by trimethylsulfonium iodide or trimethylsulfoxonium iodide and potassium fluoride/aluminum oxide.

Because it is difficult to achieve a sufficiently high yield by these conventionally known methods and, further, because these methods require complicated procedures, the present inventors contemplated improvement of the process for the preparation of azolylmethylcycloalkanol derivatives represented by formula (I), which is hereinafter described.

The present inventors have undertaken extensive studies in order to achieve this objective and found that the target compound can be produced at a high yield by carrying out a series of reactions in the preparation of the aforementioned compound (A), including an S-methylide preparation step, an epoxidation step, and an azolation step, in an organic solvent, in the presence of a metal oxide, and in the solid-liquid two-phase reaction system. This finding has led to the completion of the present invention.

SUMMARY OF THE INVENTION

Accordingly, an object of the present invention is to provide a process for preparing a derivative of azolylmethylcycloalkanol of the following formula (I) comprising, providing a solid-liquid two-phase mixture of a cycloalkanone derivative of formula (II), an azole compound of formula (III), a metal oxide of formula (IV), and an organic solvent, and adding a sulfonium compound of formula (V) to said solid-liquid two-phase mixture under heating while stirring,

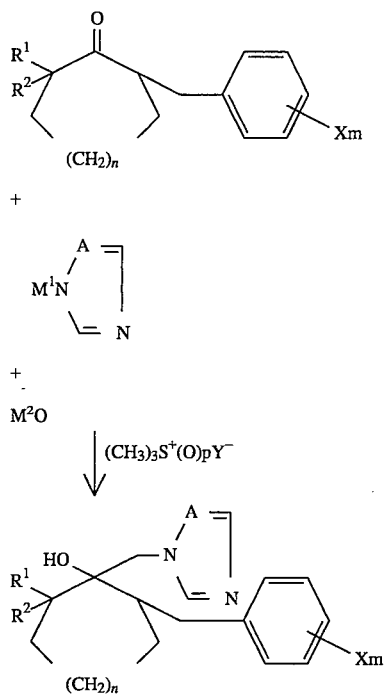

wherein $R^1$ and $R^2$ individually represent a hydrogen atom or an alkyl group; X is a halogen atom, an alkyl group, haloalkyl group, phenyl group, cyano group, or nitro group; m is an integer of 0 to 5 (when m is 2 or larger, Xs may be either the same or different); n is an integer of 0 to 2; A represents a nitrogen atom or a group CH; $M^1$ represents an alkali metal atom or an alkaline earth metal atom; $M^2$ represents an alkaline earth metal atom, a zinc atom, or two alkali metal atoms; Y represents a halogen atom or a $C_1$–$C_4$ alkoxysulfonyloxy group; and p denotes an integer of 0 or 1.

Other objects, features and advantages of the invention will hereinafter become more readily apparent from the following description.

DETAILED DESCRIPTION OF THE INVENTION AND PREFERRED EMBODIMENTS

Given as examples of preferred solvents used in the present invention are amide-type solvents, such as N,N-dimethylformamide, N,N-dimethylacetoamide, N,N-diethylacetoamide, and N-methyl-2-pyrrolidone; lower alcohols, such as methanol, ethanol, and t-butanol; and dimethylsulfoxide, and the like.

These solvents may be used either alone or as a mixture of two or more of them.

Further, the following co-solvents can be given. Aromatic hydrocarbons, such as benzene, toluene, and xylene; aliphatic hydrocarbons, such as hexane, heptane, cyclohexane, and methylcyclohexane; ethers, such as dimethoxyethane, diisopropyl ether, tetrahydrofuran, diglyme, and dioxane; and other solvents, such as acetonitrile, pyridine, picoline, hexamethylphosphoric triamide, and the like.

Given as examples of metal oxide are alkaline earth metal oxides, such as magnesium oxide, calcium oxide, and barium oxide; zinc oxide; and alkali metal oxides, such as sodium oxide and potassium oxide.

The following compounds can be given as examples of basic compounds which can be used together with the metal oxides. Alkali metal hydroxides, such as sodium hydroxide and potassium hydroxide; alkali metal carbonates, such as sodium carbonate and potassium carbonate; alkali metal alkoxides, such as sodium methoxide, sodium ethoxide, and potassium t-butoxide; alkali metal hydrides, such as sodium hydride and potassium hydride; organic alkali metal compounds such as n-butyl lithium; alkaline earth metal hydroxides, such as magnesium hydroxide and calcium hydroxide; alkaline earth metal carbonates, such as calcium carbonate and barium carbonate; alkaline earth metal alkoxides, such as magnesium methoxide and magnesium ethoxide; alkaline earth metal hydrides such as calcium hydride; organic amines, such as triethylamine, N,N-dimethylaniline, pyridine, and picoline; alkali metal salts of azole compound, such as sodium 1,2,4-triazole, potassium 1,2,4-triazole, sodium imidazole, and potassium imidazole; and alkaline earth metal salts of azole compound, such as magnesium 1,2,4-triazole and magnesium imidazole.

As examples of sulfonium compounds, trimethylsulfoxonium salts, such as trimethylsulfoxonium bromide, trimethylsulfoxonium iodide, and methyltrimethylsulfoxonium sulfate; and trimethylsulfonium salts, such as trimethylsulfonium iodide and methyltrimethylsulfonium sulfate, can be given.

In the above definition, the alkyl group of $R^1$ and $R^2$ is preferably $C_1$–$C_5$ alkyl group including methyl, ethyl, 1-methylethyl, propyl, 2-methylpropyl, butyl, 3-methylbutyl, pentyl, and the like.

The alkyl group of X is preferably $C_1$–$C_5$ alkyl group including methyl, ethyl, 1-methylethyl, propyl, 2-methylpropyl, 1,1-dimethylethyl, butyl, 3-methylbutyl, and the like. The haloalkyl represented by X are groups in which one or more hydrogen atoms in these alkyl groups are substituted by halogen atoms.

The following compounds are given as examples of cycloalkanone derivatives (II) used in the present invention.

2-(4-chlorobenzyl)cyclopentanone, 2-(4-cyanobenzyl)cyclopentanone, 2-(4-nitrobenzyl)cyclopentanone, 2-[3-(trifluoromethyl)benzyl]cyclopentanone, 2-[4-(trifluoromethyl)benzyl]cyclopentanone, 2-(4-phenylbenzyl)cyclopentanone, 5-(4-chlorobenzyl)-2,2-dimethylcyclopentanone, 5-(4-methylbenzyl)-2,2-dimethylcyclopentanone, 5-(4-phenylbenzyl)-2,2-dimethylcyclopentanone, 5-[4-(1,1-dimethylethyl)benzyl)]-2,2-dimethylcyclopentanone, 2-(4-chlorobenzyl)-5-ethylcyclopentanone, 2-(4-chlorobenzyl)-5-(1-methylethyl)cyclopentanone, 2-(4-chlorobenzyl)cyclohexanone, 6-(4-chlorobenzyl)-2,2-dimethylcyclohexanone, 2-(4-chlorobenzyl)-6-ethylcyclohexanone, 2-(4-chlorobenzyl)-6-methylcyclohexanone, 2-(4-chlorobenzyl)cycloheptanone, 7-(4-chlorobenzyl)-2,2-dimethylcycloheptanone, 2-(4-chlorobenzyl)-7-ethylcycloheptanone, and the like.

In the process of the present invention, the above-described cycloalkanone derivative of formula (II), metal salt of azole of formula (III), metal oxide of formula (IV), and sulfonium compound of formula (V) are reacted in the above-mentioned organic solvent in a solid-liquid two-phase. In this instance, the above-mentioned basic compound and co-solvent can be present together.

The target compound can be produced at a yield higher than the yields achieved by any reported conventional processes by using 1.1 mols of metal salt of azole of formula (III) and 1 mol of metal oxide of formula (IV) for 1 mol of cycloalkanone derivative of formula (II). To the extent that the reaction yield and the post treatment are not affected, the use of metal salt of azole of formula (III) and metal oxide of formula (IV) in amounts greater or smaller than 1 mol for 1 mol of cycloalkanone derivative of formula (II) falls within the scope of the present invention as a matter of course.

The sulfonium compound of formula (V) is used in an amount of 1–2 mols, preferably about 1.2–1.6 mols, for one mol of cycloalkanone derivative of formula (II).

The following procedure can be given as a preferred embodiment of the present invention.

A solid-liquid two-phase amide-type solvent mixture comprising 1.1 mols of metal salt of azole (III) and 1 mol of metal oxide (IV) for 1 mol of cycloalkanone derivative (II) is heated at about 120° C., and 1.5 mols of sulfonium compound (V) is added in portions to the mixture while stirring. After the addition, the mixture is reacted for a further 2–3 hours.

Either commercially available metal salts of azole compound or those prepared from 1,2,4-triazole or imdazole and alkali metal hydride, alkali metal alkoxide, alkaline earth metal alkoxide, or alkali metal hydroxide can be used as the metal salts of azole (III) in the present invention.

It is preferably prepared in the following manner using an alkali metal hydroxide. 1,2,4-triazole or imdazole, equivalent mol of alkali metal hydroxide, and approximately the same amount of water as the alkali metal hydroxide are added to an amide-type solvent. Toluene is added to the mixture. The mixture is then dehydrated to the water content of as small as about 1000 ppm by the toluene-water azeotropic distillation.

The method described, for example, in EP 329397 can be applied for isolating the azolylmethylcycloalkanol derivative from the reaction mixture obtained by the processes of the present invention. Specifically, the reaction mixture is cooled to room temperature, poured into ice water, and extracted with an organic solvent such as ethyl acetate, chloroform, methylene chloride, benzene, or toluene. The organic layer is separated, washed with water, and dried. The target compound is isolated from the residue obtained by evaporation of the solvent under reduced pressure.

According to the process of the present invention, the target compound can be produced at a high yield by carrying out a series of reactions in the preparation of the azolylmethylcycloalkanol derivative (I), including the S-methylide preparation step, the epoxidation step, and the azolation step, in an organic solvent, in the presence of the above-described metal oxide, and in the solid-liquid two-phase reaction system.

Other features of the invention will become apparent in the following description of the exemplary embodiment which is given for illustration of the invention and is not intended to be limiting thereof.

EXAMPLE

Preparation Example 1

Preparation of
5-(4-chlorobenzyl)-2,2-dimethyl-1-(1H-
1,2,4-triazol-1-ylmethyl)cyclopentanol 4.4 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 35 ml of toluene. The mixture was heated at 125° C. with stirring to evaporate and remove 7 ml of water from the reaction system while refluxing toluene, thus reducing the water content of the mixture in the reactor to about 1000 ppm. The reaction temperature was decreased to 115° C., and 15.3 g (0.10 mol) of barium oxide was added. After further addition of 23.68 g (0.1 mol) of 5-(4-chlorobenzyl)-2,2-dimethylcyclopentanone at the same temperature, 22.49 g (0.13 mol) of trimethylsulfoxonium bromide was added in portions over 4 hours. The mixture was heated for a further 2 hours while being stirred.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 32.50 g of an oily matter. This oily matter was purified by silica gel column chromatography, to obtain 23.04 g (yield: 72.03%) of the title compound. m.p. 113°–115° C.

Preparation Example 2

Preparation of
5-(4-chlorobenzyl)-2,2-dimethyl-1-(1H-
1,2,4-triazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Then, 5.61 g (0.10 mol) of calcium oxide was added at the same temperature, followed by the addition of 4.00 g (0.10 mol) of sodium hydroxide powder. After further addition of 23.68 g (0.1 mol) of 5-(4-chlorobenzyl)-2,2-dimethylcyclopentanone, 25.95 g (0.15 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 31.86 g of an oily matter. This oily matter was purified by silica gel column chromatography, to obtain 23.2 g (yield: 72.53%) of the title compound.

Preparation Example 3

Preparation of
5-(4-chlorobenzyl)-2,2-dimethyl-1-(1H-
1,2,4-triazol-1-ylmethyl)cyclopentanol 4.00 g (0.1 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 6.91 g (0.10 mol) of 1H-1,2,4-triazole was added and dissolved, followed by the addition of 35 ml of toluene. The mixture was heated at 125° C. with stirring to evaporate and remove 7 ml of water from the reaction system while refluxing toluene, thus reducing the water content of the mixture in the reactor to about 1000 ppm.

Then, 4.03 g (0.10 mol) of magnesium oxide was added at the same temperature, followed by the addition of 4.00 g (0.10 mol) of sodium hydroxide powder. After further addition of 23.68 g (0.1 mol) of 5-(4-chlorobenzyl)-2,2-dimethylcyclopentanone, 25.95 g (0.15 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 29.75 g of an oily matter. This oily matter was purified by silica gel column chromatography, to obtain 22.07 g (yield: 69.0%) of the title compound.

Preparation Example 4

Preparation of 5-(4-chlorobenzyl)-2,2-dimethyl-1-(1H-1,2,4-triazol-1-ylmethyl)cyclopentanol 4.00 g (0.1 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 6.91 g (0.10 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

The reaction mixture was cooled to 115° C., and 5.61 g (0.10 mol) of calcium oxide was added, followed by the addition of 4.00 g (0.10 mol) of sodium hydroxide powder. After further addition of 23.68 g (0.1 mol) of 5-(4-chlorobenzyl)- 2,2-dimethylcyclopentanone, 25.95 g (0.15 mol) of trimethylsulfoxonium bromide was added in portions over 4 hours. The mixture was heated for a further 3 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 33.76 g of an oily matter. This oily matter was purified by silica gel column chromatography, to obtain 21.28 g (yield: 66.53%) of the title compound.

Preparation Example 5

Preparation of 5-(4-chlorobenzyl)-2,2-dimethyl-1-(1H-1,2,4-triazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Then, 5.94 g (0.10 mol) of calcium oxide was added at the same temperature, followed by the addition of 5.61 g (0.10 mol) of potassium hydroxide powder. After further addition of 23.68 g (0.1 mol) of 5-(4-chlorobenzyl)- 2,2-dimethylcyclopentanone, 25.95 g (0.15 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 29.50 g of an oily matter. This oily matter was purified by silica gel column chromatography, to obtain 20.47 g (yield: 64.0%) of the title compound.

Preparation Example 6

Preparation of 5-(4-chlorobenzyl)-2,2-dimethyl-1-(1H-1,2,4-triazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 10 ml of water and 45 ml of dimethylacetamide were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 120° C. with stirring to evaporate and remove 12 ml of water from the reaction system while refluxing toluene, thus reducing the water content of the mixture in the reactor to about 1000 ppm.

Then, 15.3 g (0.10 mol) of barium oxide was added at the same temperature. After further addition of 23.68 g (0.1 mol) of 5-(4-chlorobenzyl)-2,2-dimethylcyclopentanone at the same temperature, 22.49 g (0.13 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 29.95 g of an oily matter. This oily matter was purified by silica gel column chromatography, to obtain 19.19 g (yield: 60.0%) of the title compound.

Preparation Example 7

Preparation of 5-(4-chlorobenzyl)-2,2-dimethyl-1-(1H-1,2,4-triazol-1-ylmethyl)cyclopentanol 6.17 g (0.11 mol) of potassium hydroxide was charged in a 200 ml four-necked flask equipped with a condenser with a calcium chloride tube, a stirrer, a thermometer, a nitrogen inlet tube, and a water trap. 10 ml of water and 45 ml of N-methyl-2-pyrrolidone were added, and the mixture was stirred to dissolve the potassium hydroxide. Then, 7.60 g (0.11 mol) of 1H-1,2,4-triazole was added and dissolved, followed by the addition of 40 ml of toluene. The mixture was heated at 125° C. with stirring to evaporate and remove 12 ml of water from the reaction system while refluxing toluene, thus reducing the water content of the mixture in the reactor to about 1000 ppm.

Then, 5.61 g (0.10 mol) of calcium oxide was added at the same temperature, followed by the addition of 4.0 g (0.10 mol) of sodium hydroxide powder. After further addition of 23.68 g (0.1 mol) of 5-(4-chlorobenzyl)-2,2-dimethylcyclopentanone, 25.95 g (0.15 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 30.50 g of an oily matter. This oily matter was purified by silica gel column chromatography, to obtain 23.0 g (yield: 72.0%) of the title compound.

Preparation Example 8

Preparation of 5-(4-chlorobenzyl)-2,2-dimethyl-1-(1H-1,2,4-triazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Then, 5.61 g (0.10 mol) of calcium oxide and 15.3 g (0.10 mol) of barium oxide were added at the same temperature. After further addition of 23.68 g (0.1 mol) of 5-(4-chlorobenzyl)-2,2-dimethylcyclopentanone, 25.95 g (0.15 mol) of trimethylsulfoxonium bromide was added in portions over 4 hours. The mixture was heated for a further 2 hours while stirring.

After the reaction, the the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 33.57 g of an oily matter. This oily matter was purified by silica gel column chromatography, to obtain 23.35 g (yield: 73.0%) of the title compound.

Preparation Example 9

Preparation of 5-(4-chlorobenzyl)-2,2-dimethyl-1-(1H-imidazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.49 g (0.11 mol) of 1H-imidazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Then, 5.61 g (0.10 mol) of calcium oxide was added at the same temperature, followed by the further addition of 4.00 g (0.10 mol) of sodium hydroxide powder. After adding 23.68 g (0.1 mol) of 5-(4-chlorobenzyl)-2,2-dimethylcyclopentanone, 25.95 g (0.15 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with ethyl acetate, and the extract was washed with water. The ethyl acetate layer was dried over anhydrous sodium sulfate and ethyl acetate was evaporated under reduced pressure to obtain 32.0 g of an oily matter. This oily matter was purified by silica gel column chromatography, to obtain 22.64 g (yield: 71.0%) of the title compound. m.p. 130°–132° C.

Preparation Example 10

Preparation of 5-(4-chlorobenzyl)-2,2-dimethyl-1-(1H-imidazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.49 g (0.11 mol) of 1H-imidazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Next, the reaction mixture was cooled to 115° C., 15.3 g (0.10 mol) of barium oxide were added. After the addition of 23.68 g (0.1 mol) of 5-(4-chlorobenzyl)-2,2-dimethylcyclopentanone, 22.4 g (0.13 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with ethyl acetate, and the extract was washed with water. The ethyl acetate layer was dried over anhydrous sodium sulfate and ethyl acetate was evaporated under reduced pressure to obtain 32.50 g of an oily matter. This oily matter was purified by silica gel column chromatography, to obtain 23.28 g (yield: 73.0%) of the title compound.

Preparation Example 11

Preparation of 2-(4-chlorobenzyl)-5-(1-methylethyl)-1-(1H-1,2,4-triazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Next, 5.61 g (0.10 mol) of calcium oxide was added at the same temperature, followed by the addition of 4.0 g (0.10 mol) of sodium hydroxide powder. After the addition of 25.08 g (0.1 mol) of 2-(4-chlorobenzyl)-5-(1-methylethyl)cyclopentanone, 25.95 g (0.15 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 33.44 g of an oily matter. This oily matter was purified by silica gel column chromatography, to obtain 23.3 g (yield: 70.0%) of the title compound.

Preparation Example 12

Preparation of 2-(4-chlorobenzyl)-5-(1-methylethyl)-1-(1H-1,2,4-triazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Next, 15.3 g (0.10 mol) of barium oxide was added at the same temperature. After the addition of 25.08 g (0.1 mol) of 2-(4-chlorobenzyl)-5-(1-methylethyl)cyclopentanone, 22.49 g (0.13 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 32.86 g of an oily matter. This oily matter was purified by silica gel column chromatography, to obtain 23.98 g (yield: 72.0%) of the title compound.

Preparation Example 13

Preparation of 2-(4-chlorobenzyl)-1-(1H-1,2,4-triazol-1-ylmethyl)cyclohexanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Next, 5.61 g (0.10 mol) of calcium oxide was added at the same temperature, followed by the further addition of 4.0 g (0.10 mol) of sodium hydroxide powder. After the addition of 22.27 g (0.1 mol) of 2-(4-chlorobenzyl)cyclohexanone, 25.99 g (0.15 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 32.51 g of an oily matter. This oily matter was purified by silica gel column chromatography, to obtain 23.2 g (yield: 65.0%) of the title compound.

Preparation Example 14

Preparation of 2-(4-chlorobenzyl)-1-(1H-1,2,4-triazol-1-ylmethyl)cycloheptanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Next, 15.3 g (0.10 mol) of barium oxide was added at the same temperature. After the addition of 23.68 g (0.1 mol) of 2-(4-chlorobenzyl)cycloheptanone, 22.49 g (0.13 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 29.44 g of an oily matter. This oily matter was purified by silica gel column chromatography, to obtain 20.79 g (yield: 65.0%) of the title compound.

Preparation Example 15

Preparation of 2-(4-phenylbenzyl)-1-(1H-1,2,4-triazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Next, 15.3 g (0.10 mol) of barium oxide was added at the same temperature. After the addition of 24.80 g (0.1 mol) of 2-(4-phenylbenzyl)cyclopentanone, 22.49 g (0.13 mol) of trimethylsulfoxonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 30.53 g of an oily matter. This oily matter was purified by silica gel column chromatography, to obtain 22.57 g (yield: 68.0%) of the title compound. m.p. 145°–148° C.

Preparation Example 16

Preparation of 2,2-dimethyl-5-(4-methylbenzyl)-1-(1H-1,2,4-triazol-1-ylmethyl)cyclopentanol 4.40 g (0.11 mol) of sodium hydroxide was charged in a 200 ml four-necked flask equipped with a condenser with a calcium chloride tube, a stirrer, a thermometer, a nitrogen inlet tube, and a water trap. 5 ml of water and 45 ml of N-methyl-2-pyrrolidone were added, and the mixture was stirred to dissolve the sodium hydroxide. Then, 7.60 g (0.11 mol) of 1H-1,2,4-triazole was added and dissolved, followed by the addition of 40 ml of toluene. The mixture was heated at 125° C. with stirring to evaporate and remove 7 ml of water from the reaction system while refluxing toluene, thus reducing the water content of the mixture in the reactor to about 1000 ppm.

Next, 15.3 g (0.10 mol) of barium oxide was added at the same temperature. After the addition of 21.60 g (0.1 mol) of 2,2-dimethyl-5-(4-methylbenzyl)cyclopentanone, 22.49 g (0.13 mol) of trimethylsulfonium bromide was added in portions over 4 hours. The mixture was heated for a further 2 hours while stirring.

After the reaction, the reaction mixture was cooled to room temperature and the precipitate was separated by filtration. The filtrate was poured into ice water and extracted with toluene, and the extract was washed with water. The toluene layer was dried over anhydrous sodium sulfate and toluene was evaporated under reduced pressure to obtain 29.87 g of an oily matter. This oily matter was purified by silica gel column chromatography, to obtain 20.99 g (yield: 70.0%) of the title compound. m.p. 118°–120° C.

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing a derivative of azolylmethyl-cycloalkanol of the following formula (I) comprising, providing a solid-liquid two-phase mixture of a cycloalkanone derivative of formula (II), an azole compound of formula (III), a metal oxide of formula (IV), and an organic solvent, and adding a sulfonium compound of formula (V) to said solid-liquid two-phase mixture under heating while stirring,

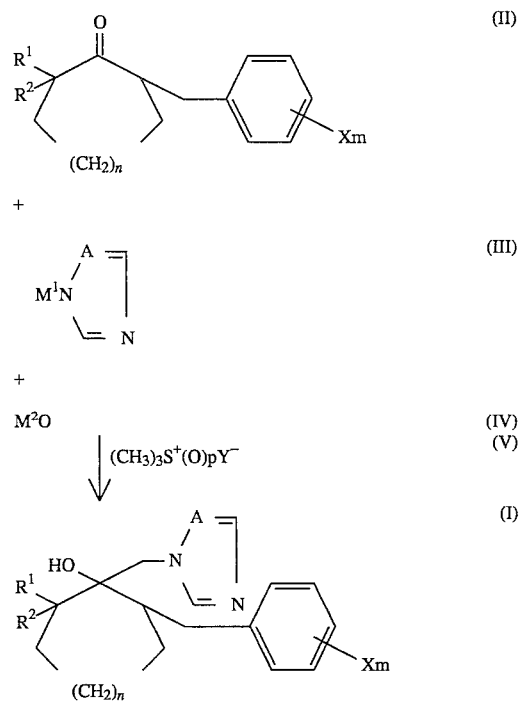

wherein $R^1$ and $R^2$ individually represent a hydrogen atom or an alkyl group; X is a halogen atom, an alkyl group, a haloalkyl group, a phenyl group, a cyano group, or a nitro group; m is an integer of 0 to 5; n is an integer of 0 to 2 (when m is 2 or larger, Xs may be either the same or different); A represents a nitrogen atom or a group CH; $M^1$ represents an alkali metal atom or an alkaline earth metal atom; $M^2$ represents an alkaline earth metal atom, a zinc atom, or two alkali metal atoms; Y represents a halogen atom or a $C_1$–$C_4$ alkoxysulfonyloxy group; and p denotes an integer of 0 or 1.

2. The process according to claim 1, wherein $R^1$ and $R^2$ individually represent a hydrogen atom or a $C_1$–$C_5$ alkyl group; X is a halogen atom, a $C_1$–$C_5$ alkyl group, or a phenyl group; m is an integer of 0 to 2 (when m is 2, Xs may be either the same or different); $M^1$ is a sodium or potassium atom; $M^2$ represents a magnesium atom, a calcium atom, a barium atom, a zinc atom, two sodium atoms, or two potassium atoms; and Y represents a bromine or iodine atom, or methoxysulfonyloxy group.

3. The process according to claim 1, wherein said organic solvent is one or more organic solvents selected from the group consisting of N,N-dimethylformamide, N,N-dimethylacetoamide, N,N-diethylacetoamide, and N-methyl-2-pyrrolidone, methanol, ethanol, t-butanol, and dimethylsulfoxide.

4. The process according to claims 1 or 2, wherein said sulfonium compound of formula (V) is trimethylsulfoxonium bromide, trimethylsulfoxonium iodide, and methyltrimethylsulfoxonium sulfate, trimethylsulfonium iodide, or methyltrimethylsulfonium sulfate.

* * * * *